(12) United States Patent
Tenley et al.

(10) Patent No.: US 7,190,162 B2
(45) Date of Patent: Mar. 13, 2007

(54) METHODS AND APPARATUS FOR INSPECTING A COMPONENT

(75) Inventors: Brenda Catherine Tenley, Liberty Township, OH (US); Michael Leonard Dziech, Cincinnati, OH (US); Joseph Anthony Traxler, Fairfield Township, OH (US)

(73) Assignee: General Electric Company, Schenectady, NY (US)

( * ) Notice: Subject to any disclaimer, the term of this patent is extended or adjusted under 35 U.S.C. 154(b) by 223 days.

(21) Appl. No.: 10/898,080

(22) Filed: Jul. 23, 2004

(65) Prior Publication Data

US 2006/0017434 A1  Jan. 26, 2006

(51) Int. Cl.
G01N 27/87 (2006.01)
G01N 27/90 (2006.01)
G01R 33/00 (2006.01)

(52) U.S. Cl. .................. 324/238; 324/262
(58) Field of Classification Search ............ 324/219, 324/220, 221, 228, 234, 239, 240, 241, 260, 324/261, 262; 73/866.5
See application file for complete search history.

(56) References Cited

U.S. PATENT DOCUMENTS

| | | | |
|---|---|---|---|
| 4,598,469 A | 7/1986 | Weixel | |
| 4,629,984 A * | 12/1986 | Scalese | 324/228 |
| 4,644,274 A * | 2/1987 | Casarcia | 324/262 |
| 4,864,239 A | 9/1989 | Casarcia et al. | |
| 5,345,514 A | 9/1994 | Mahdavieh et al. | |
| 5,465,045 A | 11/1995 | DeRock | |
| 5,670,879 A | 9/1997 | Zombo et al. | |
| 6,175,234 B1 | 1/2001 | Granger, Jr. et al. | |
| 6,414,480 B1 | 7/2002 | Traxler | |
| 6,426,622 B1 | 7/2002 | Givens et al. | |
| 6,479,989 B2 * | 11/2002 | Taylor | 324/219 |
| 6,545,469 B1 | 4/2003 | Batzinger et al. | |
| 6,608,478 B1 | 8/2003 | Dziech et al. | |
| 6,696,830 B2 | 2/2004 | Casarcia et al. | |
| 2002/0079889 A1 | 6/2002 | Givens et al. | |

FOREIGN PATENT DOCUMENTS

| | | |
|---|---|---|
| EP | 1217370 | 6/2002 |
| EP | 05254259 | 11/2005 |

* cited by examiner

*Primary Examiner*—Edward Lefkowitz
*Assistant Examiner*—Kenneth J. Whittington
(74) *Attorney, Agent, or Firm*—William Scott Andes; Armstrong Teasdale LLP (57) ABSTRACT

A method for inspecting a gas turbine engine rotor disk, wherein the rotor disk includes a plurality of dovetail slots, includes providing a probe assembly including an eddy current probe and a probe fixture, wherein the eddy current probe includes a body portion and a tip portion including an eddy current probe coil. The method also includes inserting the eddy current probe into the probe fixture, coupling the probe fixture to the rotor disk such that at least a portion of the probe fixture is coupled to at least one of the dovetail slots, and such that the eddy current probe is positioned adjacent the rotor disk, generating an eddy current in the rotor disk using the eddy current probe coil, and inspecting the rotor disk using the probe assembly.

19 Claims, 4 Drawing Sheets

METHODS AND APPARATUS FOR INSPECTING A COMPONENT

BACKGROUND OF THE INVENTION

This invention relates generally to the inspecting of components, and more particularly to methods and apparatus for inspecting components having non-uniform surfaces.

Eddy current (EC) inspection devices are used to detect abnormal indications in a component under test such as, but not limited to, a gas turbine engine component. At least one known EC inspection device is used to detect cracks, pings, dings, raised material, and/or other surface imperfections on a surface of the component and/or to evaluate material properties of the component including the conductivity, density, and/or degrees of heat treatment of the component.

At least one known EC device measures the interaction between an electromagnetic field generated by the EC device and the component to be inspected. For example, the EC device includes a probe coil that generates a magnetic field. When the coil/field is positioned proximate to a conductive component, an eddy current is generated on the surface of the component. A flaw on and/or near the surface of the component generates a disruption in the eddy current field which produces a secondary field that is received by the eddy current probe coil or by a sensor coil in the eddy current probe which converts the altered secondary magnetic field to an electrical signal which may be recorded on a strip chart for example.

At least one known EC device includes a relatively small coil, that is typically 0.020 inches in diameter, that is used to detect surface flaws, surface contamination, material properties, and/or a surface roughness of the component being inspected. In use, the coil is positioned normal to the surface of the component under test. A substantially constant pressure is applied to the probe as the coil is moved along the surface of the component under test to facilitate maintaining an integrity of the signal generated by the EC device. However, when the EC device is not oriented normal to the surface of the component being inspected, a "lift-off effect" may be created When a non-continuous surface feature needs to be inspected, such as a feature on a rotating part, known differential probes may have difficulty resolving sharp curvatures, such as in chamfers, corners and/or cusps. During operation, when such differential probes encounter a chamfer, corner or cusp, the differential probe device may become skew to the surface of the component, such that a resulting lift-off effect may cause a loss of usable data. Accordingly, known EC devices may be less effective in generating an accurate response when the EC device is used to detect an abnormal condition on a component having complex geometries, and/or a component having irregular conditions such that the probe cannot consistently be placed normal to scan surface.

BRIEF DESCRIPTION OF THE INVENTION

In one aspect, a method is provided for inspecting a gas turbine engine rotor disk, wherein the rotor disk includes a plurality of dovetail slots. The method includes providing a probe assembly including an eddy current probe and a probe fixture, wherein the eddy current probe includes a body portion and a tip portion including an eddy current probe coil. The method also includes inserting the eddy current probe into the probe fixture, coupling the probe fixture to the rotor disk such that at least a portion of the probe fixture is coupled to at least one of the dovetail slots, and such that the eddy current probe is positioned adjacent the rotor disk, generating an eddy current in the rotor disk using the eddy current probe coil, and inspecting the rotor disk using the probe assembly.

In another aspect, a probe assembly is provided for inspecting a gas turbine engine rotor disk, wherein the rotor disk includes a plurality of dovetail slots. The probe assembly includes an eddy current probe including a body portion, a tip portion extending from the body portion, and an eddy current probe coil mounted within the tip portion. The tip portion is configured to be positioned adjacent the rotor disk such that the probe coil generates a magnetic field that is substantially perpendicular to a surface of the rotor disk being inspected. The probe assembly also includes a probe fixture configured to be coupled to at least one dovetail slot and to the probe fixture such that the tip portion is positioned adjacent the rotor disk when the probe fixture is securely coupled to the at least one dovetail slot.

In yet another aspect, a probe fixture is provided for positioning an eddy current probe adjacent a rotor disk, wherein the rotor disk includes a plurality of dovetail slots, and the eddy current probe includes an eddy current probe coil configured to be positioned adjacent the rotor disk for inspecting the rotor disk. The probe fixture includes a platform including a first surface and a second surface, and an extension arm extending outward from the first surface. The eddy current probe is coupled to the extension arm. The probe fixture also includes a first leg and a second leg each extending outwardly from the second surface such that at least one of the first and second legs is configured to be coupled to a portion of the rotor disk.

DETAILED DESCRIPTION OF THE INVENTION

Figure 1:
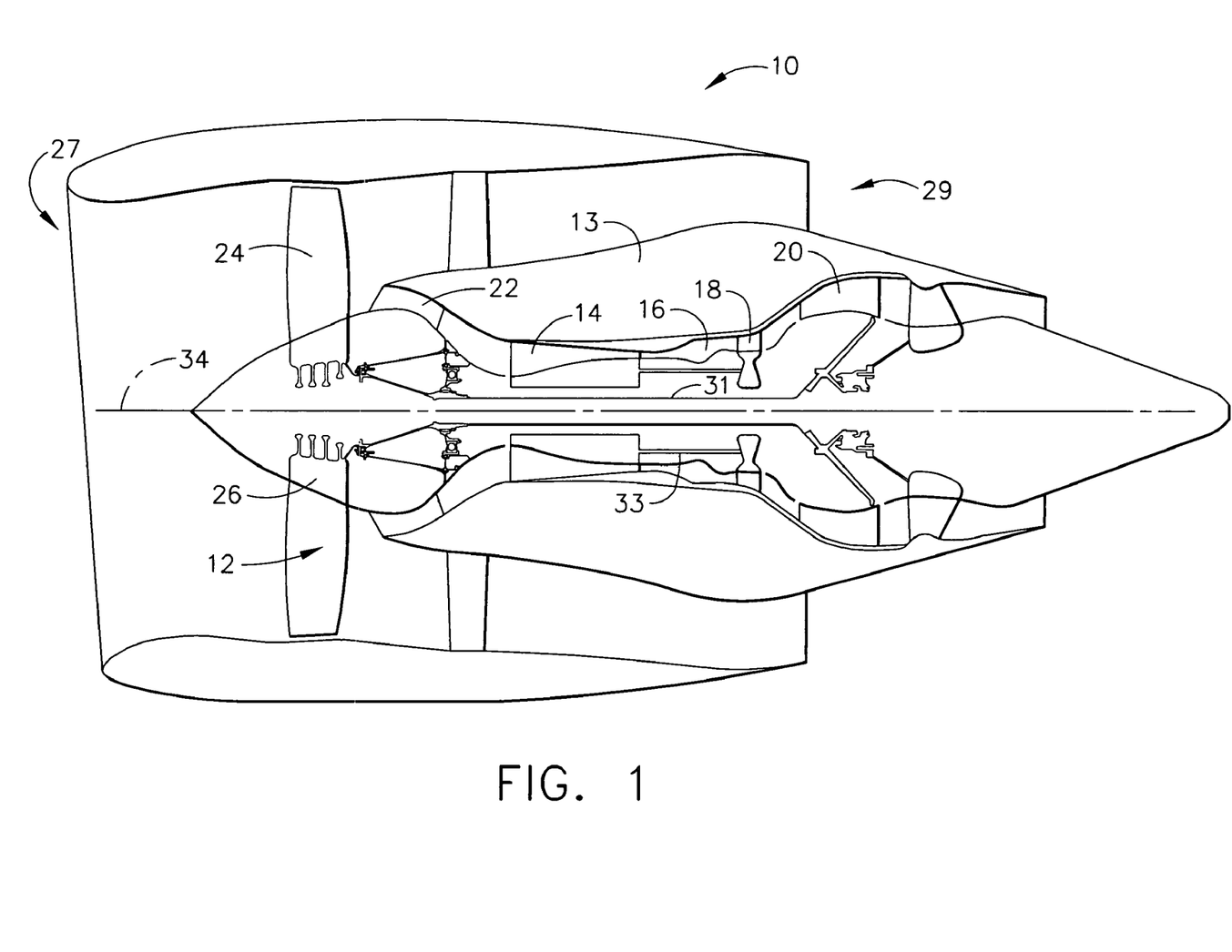
FIG. 1 is a schematic illustration of an exemplary gas turbine engine.

FIG. 1 is a schematic illustration of a gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a CF6-50 available from General Electric Company, Cincinnati, Ohio. Fan assembly 12 and turbine 20 are coupled by a first rotor shaft 31, and compressor 14 and turbine 18 are coupled by a second rotor shaft 33.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 2:
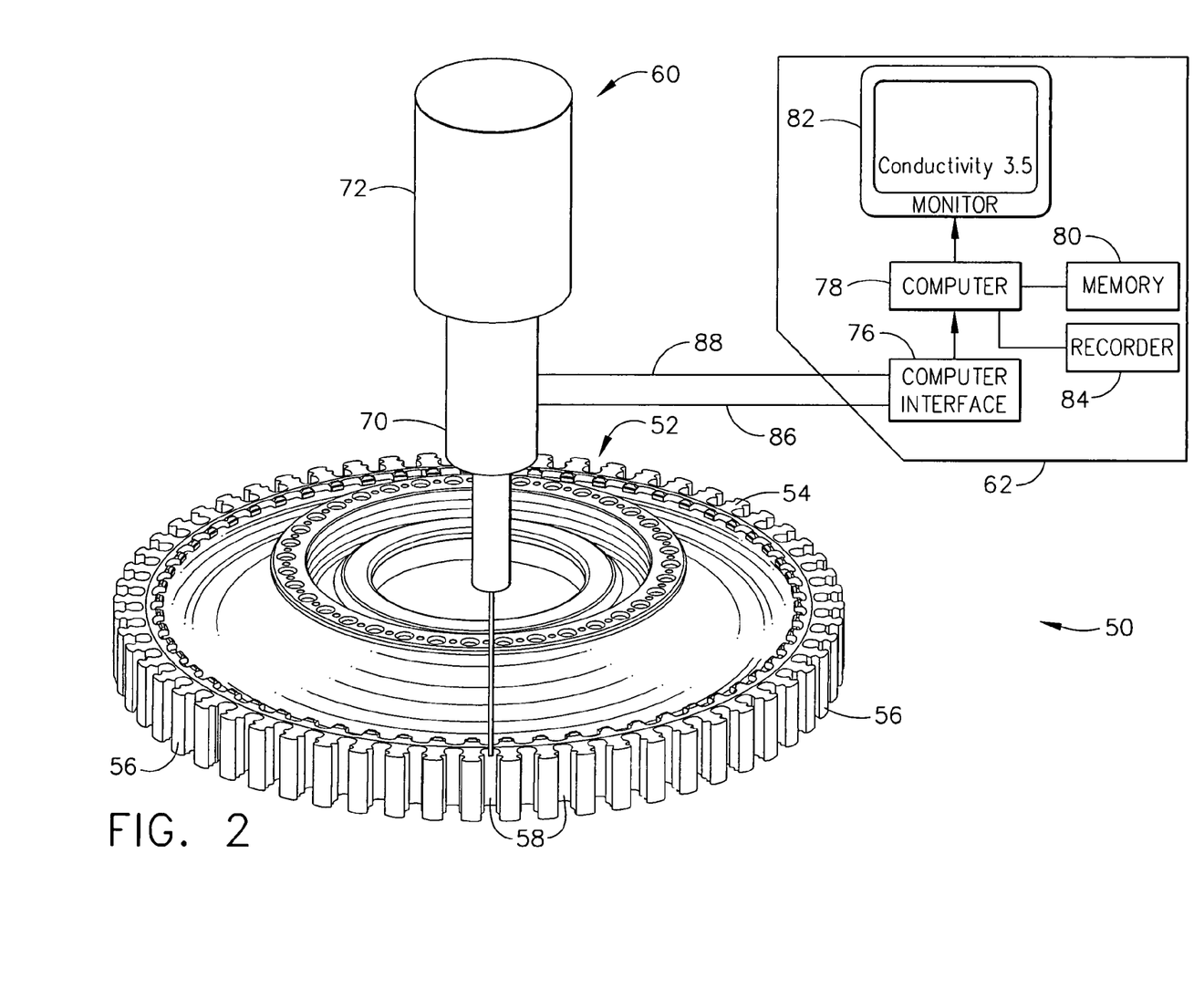
FIG. 2 is a schematic diagram of an exemplary eddy current surface flaw detection system.

FIG. 2 is a schematic diagram of an exemplary eddy current surface flaw detection system 50 that can be used to inspect a component 52 such as, but not limited to, a gas turbine engine disk 54 which may be used with gas turbine engine 10. In the exemplary embodiment, engine disk 54 includes a plurality of gear teeth 56 and a plurality of dovetail slots 58 defined between gear teeth 56.

Although the methods and apparatus herein are described with respect to gear teeth 56 and dovetail slots 58, it should be appreciated that the methods and apparatus can be applied to a wide variety of components. For example, component 52 may be of any operable shape, size, and configuration. Examples of such components may include, but are not limited to, components of gas turbine engines, such as seals, flanges, turbine blades, turbine vanes, and/or flanges. The component may be fabricated from any operable base material, such as, but not limited to, nickel-base alloys, cobalt-base alloys, titanium-base alloys, iron-base alloys, and/or aluminum-base alloys, In the exemplary embodiment, detection system 50 includes a probe assembly 60 and a data acquisition/control system 62. Probe assembly 60 includes an eddy current coil/probe 70 and a probe fixture 72. Eddy current probe 70 is electrically coupled to data acquisition/control system 62 such that control/data information can be transmitted to/from eddy current probe 70 and data acquisition/control system 62. In an alternative embodiment, system 50 also includes a turntable (not shown) configured to rotate component 52 around a central axis 74 during the inspection procedure.

Data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that should be familiar to those skilled in the art. Examples of such storage facilities often used with computer 78 include, but are not limited to, solid state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to, or external to, computer 78. Data acquisition/control system 62 also includes a recording device 84 such as, but not limited to, a strip chart recorder, a C-scan, and an electronic recorder, that is electrically coupled to either computer 78 and/or eddy current probe 70.

In use, component 52, such as disk 54, is mounted on a fixture (not shown) to secure disk 54 in place during inspection. Eddy current probe 70 is coupled to probe fixture 72 to position and/or secure probe 70 within a portion of component 52, such as, but not limited to, dovetail slot 58 such that probe 70 facilitates enabling a portion of dovetail slot 58 to be scanned during inspection. Specifically, in one embodiment, eddy current probe 100 scans a chamfer region of a dovetail slot bottom. In the exemplary embodiment, eddy current probe 70 is electrically coupled to data acquisition/control system 62 by a data link 86. Eddy current probe 70 generates electrical signals in response to the eddy currents induced within the surface of dovetail slots 58 during scanning of dovetail slots 58 by probe 70. Electrical signals generated by probe 70 are received by data acquisition/control system 62 over a data communications link 86 and are either stored in memory 80 or recording device 84. In one embodiment, computer 78 is also interconnected to probe assembly 60 by a communications link 88 to facilitate controlling the scanning of dovetail slots 58. A keyboard (not shown) is electrically coupled to computer 78 to facilitate operator control of the inspection of disk 54. In the exemplary embodiment, a printer 40 is provided to generate hard copies of the images generated by computer 78.

Figure 3:
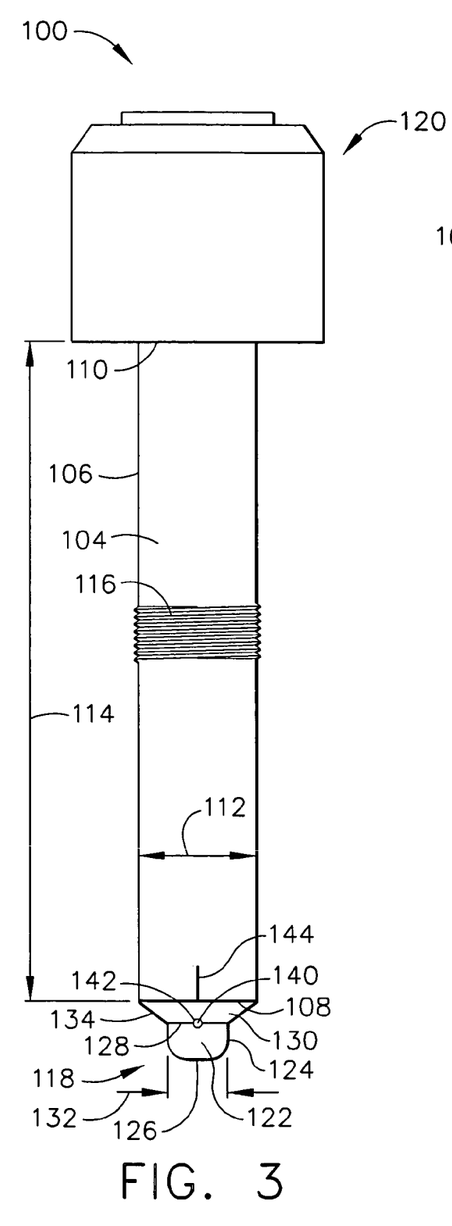
FIG. 3 is a side view of an exemplary eddy current probe.
Figure 4:
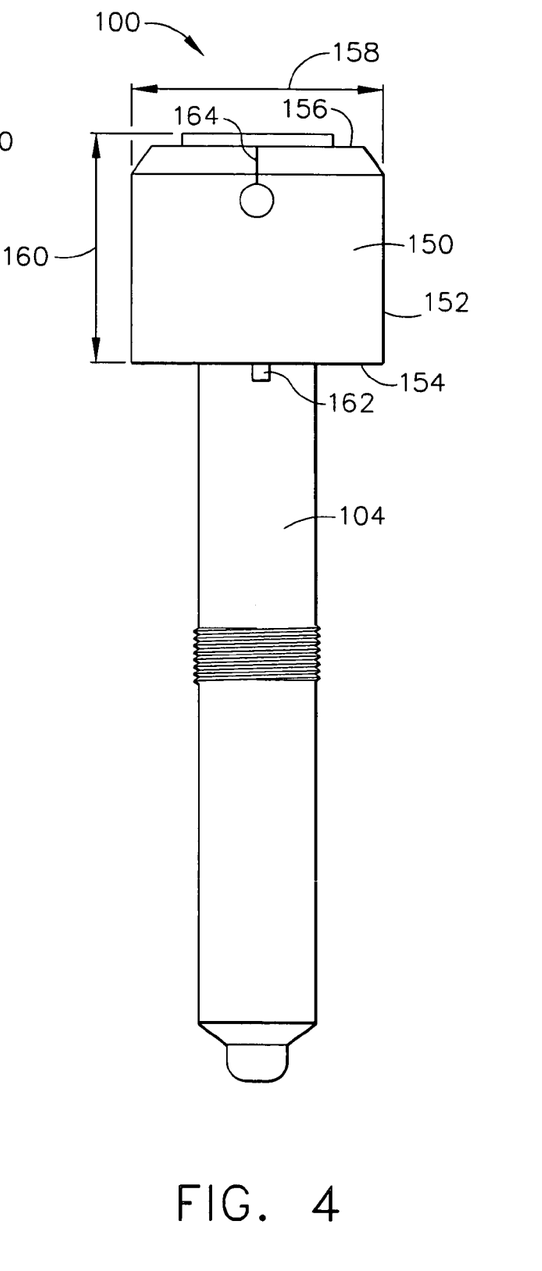
FIG. 4 is another side view of the eddy current probe shown in FIG. 3.
Figures 5, 6:
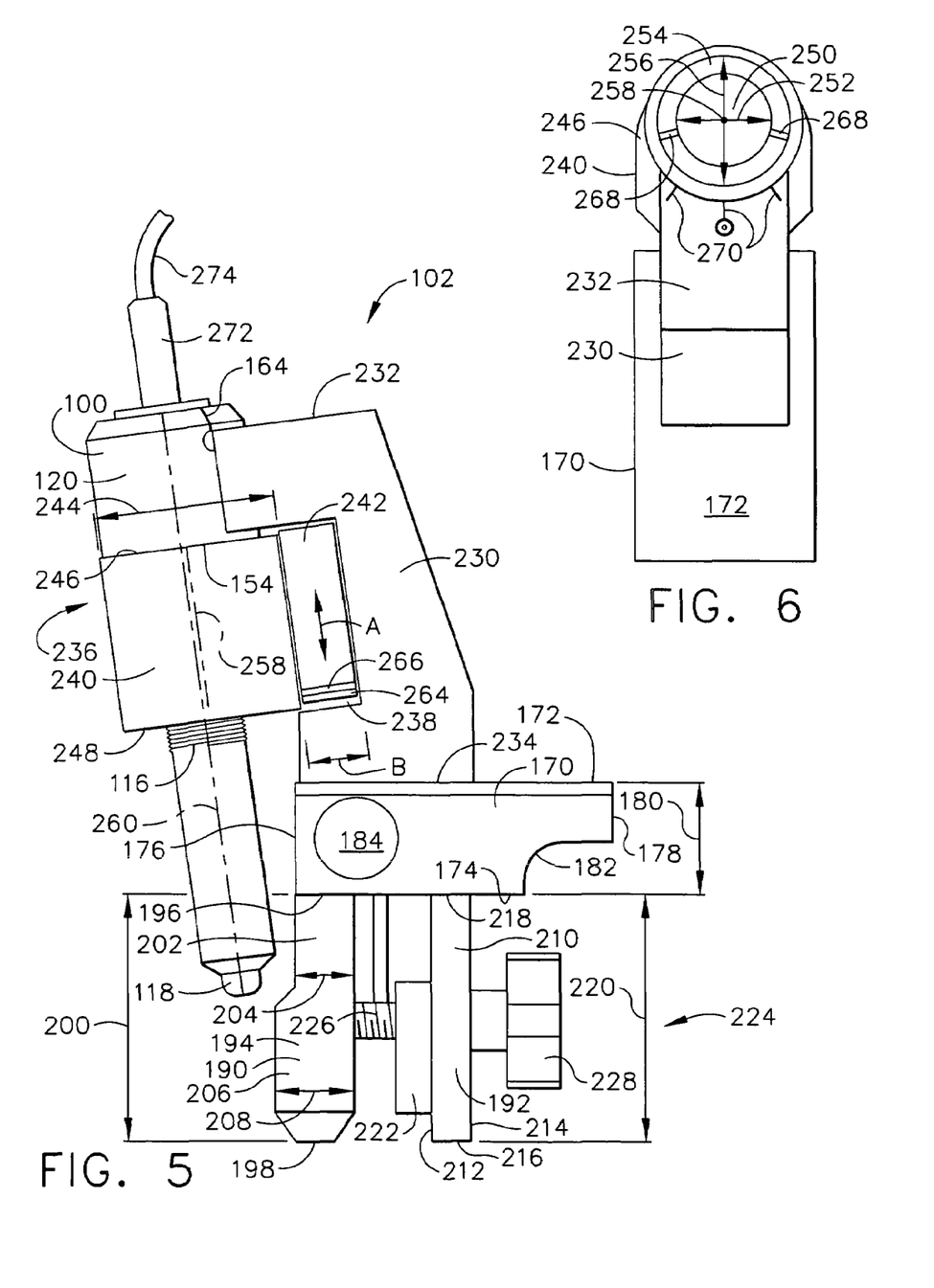
FIG. 5 is a side view of an exemplary probe assembly including the eddy current probe shown in FIG. 3.
FIG. 6 is a top view of the probe assembly shown in FIG. 5.

FIG. 3 is a side view of an exemplary eddy current probe 100 that may be used with eddy current surface flaw detection system 50 (shown in FIG. 2). FIG. 4 is an opposing side view of eddy current probe 100. FIG. 5 is a side view of probe assembly 60 including probe 100 and an exemplary probe fixture 102. FIG. 6 is a top view of a portion of probe fixture 102.

Eddy current probe 100 includes a body portion 104 that includes an outer surface 106 extending between a first end 108 and a second end 110. Body portion 104 has a width 112 and a length 114 that is different than width 112. In the exemplary embodiment, body portion 104 is substantially cylindrical shaped to facilitate rotating probe 100 within probe fixture 102. Moreover, body portion 104 includes a band 116 extending radially outward from body outer surface 106. Band 116 facilitates supporting and/or aligning probe 100 within probe fixture 102.

Eddy current probe 100 also includes a tip portion 118 and a base portion 120 that are coupled to body portion 104. Specifically, tip portion 118 is coupled to body first end 108, and base portion 120 is coupled to body second end 110. In the exemplary embodiment, body portion 104, tip portion 118, and base portion 120 are integrally formed together such that body portion 104, tip portion 118, and base portion 120 form a unitary eddy current probe 100. In an alternative embodiment, body portion 104, tip portion 118, and base portion 120 are coupled together to form eddy current probe 100.

Tip portion 118 includes a positioning tip 122 that includes an outer surface 124 extending between a first end 126 and a second end 128, and a tip chamfer portion 130. Specifically, tip chamfer portion 130 extends between body first end 108 and tip second end 128. Moreover, positioning tip 122 has a width 132 that is shorter than base portion width 112 such that an outer surface 134 of tip chamfer portion 130 extends between body outer surface 106 and tip outer surface 124.

As illustrated in FIG. 3, eddy current probe 100 includes a probe coil 140 mounted within tip portion 118. Specifically, probe coil 140 is positioned adjacent positioning tip second end 128. Probe coil 140 includes a substantially cylindrical outer surface 142 such that at least a portion of probe coil 140 is positioned proximate to tip chamfer portion 130. In the exemplary embodiment, probe coil 140 is a side mount coil. When activated, coil 140 generates a magnetic field that is substantially perpendicular to a surface of component 52 being scanned such as, but not limited to gear teeth 56 and dovetail slots 58 (shown in FIG. 2). More specifically, probe coil 140 transmits a transient electromagnetic flux into the metallic object under test. In one embodiment, probe 100 includes a scribe line 144 that is generally aligned with probe coil 140. Scribe line 144 facilitates visually aligning probe 100 within probe fixture 102 and/or dovetail slots 58.

Base portion 120 includes a body 150 that includes an outer surface 152 extending between a first end 154 and a second end 156. Base portion body 150 includes a width 158 and a length 160. Base portion width 158 is longer than body portion width 112 to facilitate supporting and/or aligning probe 100 within probe fixture 102. In the exemplary embodiment, body 150 is substantially cylindrical shaped to facilitate rotating probe 100 within probe fixture 102. As illustrated in FIG. 4, base portion 120 also includes a locating pin 162 extending from base portion first end 154. Locating pin 162 facilitates positioning probe 100 within probe fixture 102 when probe 100 is inserted into probe fixture 102. In one embodiment, base portion 120 includes a scribe line 164 to facilitate visually aligning probe 100 within probe fixture 102. Scribe line 164 is generally aligned with locating pin 162.

Probe fixture 102 includes a fixture platform 170 having a first surface 172, a second surface 174, a first end 176, and a second end 178. First surface 172 and second surface 174 are planar and oriented generally parallel with respect to one another such that first and second surfaces 172 and 174 are separated by a distance 180. Fixture platform 170 includes a recessed area 182 and a divot 184 to facilitate gripping, moving, and/or handling probe fixture 102 by a user.

Probe fixture 102 also includes a first leg 190 and a second leg 192 extending outwardly from platform second surface 174. Legs 190 and 192 cooperate to securely couple probe fixture 102 in position with respect to disk 54. Specifically, a portion of disk 54, such as gear teeth 56, are inserted tightly between first leg 190 and second leg 192 such that probe assembly 60 remains in a substantially fixed position during the inspecting of component 52. In the exemplary embodiment, first leg 190 is fixed with respect to platform 170 and is positioned adjacent platform first end 176. First leg 190 includes a body 194 extending between a first end 196 and a second end 198 for a length 200. In one embodiment, first leg 190 is chamfered at second end 198 to facilitate loading probe fixture 102 within a portion of component 52, such as, but not limited to, dovetail slot 58. Length 200 is selected to facilitate securing probe fixture 102 to disk 54. In the exemplary embodiment, first leg 190 is sized and shaped to facilitate positioning first leg 190 within disk 54, particularly within dovetail slot 58 between gear teeth 56. In one embodiment, first leg 190 is cylindrical and includes an upper portion 202 having a first diameter 204 and a lower portion 206 having a second diameter 208, wherein first diameter 204 is shorter than second diameter 208.

Second leg 192 includes a body 210 having an inner surface 212 and an outer surface 214 that extend between a first end 216 and a second end 218 for a length 220. Length 220 is selected to facilitate securing probe fixture 102 to disk 54. Moreover, second leg 192 is moveable with respect to platform 170 and fixed first leg 190, such that second leg 192 is variably positioned along second surface 174 between first leg 190 and platform second end 178. As such, second leg 192 facilitates securing probe fixture 102 to disk 54. In one embodiment, first leg 190 is positioned in a dovetail slot 58 and second leg 192 is repositioned to contact adjacent gear teeth 56 such that a portion of each gear tooth 56 is positioned between first leg 190 and second leg 192. In another embodiment, one gear tooth 56 is positioned between first leg 190 and second leg 192. In the exemplary embodiment, a spacer 222 is coupled to inner surface 212 such that spacer 222 is positioned between second leg 192 and gear teeth 56. In one embodiment, spacer 222 is fabricated from a partially compressible material, such as, but not limited to, rubber to facilitate protecting second leg 192 and/or gear teeth 56 from damage and wear.

In the exemplary embodiment, an adjustment mechanism 224 is coupled to second leg 192 to reposition second leg 192 either towards or away from first leg 190 to securely couple or uncouple probe fixture 102 to rotor disk 54. In one embodiment, adjustment mechanism 224 includes a threaded rod 226 extending through second leg 192 into first leg 190, and a knob 228 is coupled to one end of threaded rod 226. In use, as knob 228 is rotated in a clockwise direction, second leg 192 is moved relatively closer to first leg 190. Alternatively, as knob 228 is rotated in a counter-clockwise direction, second leg 192 is moved relatively away from first leg 190.

Probe fixture 102 also includes an extension arm 230 that includes an upper surface 232 and a lower surface 234. Extension arm 230 extends outwardly from platform first surface 172. Extension arm 230 facilitates supporting eddy current probe 100 in position relative to component 52 during inspecting of component 52. In one embodiment, extension arm 230 extends obliquely from platform first surface 172 to facilitate positioning probe 100 with respect to component 52. In the exemplary embodiment, extension arm 230 includes a probe holder assembly 236 positioned within a slot 238 of extension arm 230. In use, eddy current probe 100 is inserted into probe holder assembly 236 and positioned such that, when probe fixture 102 is coupled to component 52, probe positioning tip 122 is positioned adjacent a portion of component 52 such as, but not limited to, a disk break edge or chamfer region.

In the exemplary embodiment, probe holder assembly 236 includes a probe holder 240 and an actuating mechanism 242. Probe holder 240 is coupled to and extends outwardly from actuating mechanism 242 for a distance 244. Distance 244 is variably selected to facilitate positioning probe 100 with respect to component 52. In the exemplary embodiment, probe holder 240 includes an upper surface 246 and a lower surface 248. As shown in FIG. 6, a bore 250 extends through probe holder 240 from upper surface 246 to lower surface 248. Bore 250 is sized to receive eddy current probe 100. Specifically, bore 250 has a width 252 that is substantially similar to probe body width 112. Moreover, bore 250 includes a shoulder 254 to facilitate supporting probe locating pin 162 when probe 100 is loaded into probe fixture 102. Shoulder 254 has a width 256 that is longer than bore width 252. In the exemplary embodiment, bore 250 includes a central axis 258 that is substantially aligned with a probe central axis 260 extending through eddy current probe 100 when probe 100 is inserted into probe holder 240.

In the exemplary embodiment, actuating mechanism 242 is coupled between probe holder 240 and extension arm 230. Moreover, actuating mechanism 242 is coupled to extension arm 230 within slot 238. In the exemplary embodiment, actuating mechanism 242 includes a first alignment assembly 264 and a second alignment assembly 266. First alignment assembly 264 facilitates aligning probe holder 240 and/or eddy current probe 100 in a substantially linear y-axis direction, particularly in the direction of arrow A. Second alignment assembly 266 facilitates aligning probe holder 240 and/or eddy current probe 100 in a substantially linear x-axis direction, particularly in the direction of arrow B. Moreover, alignment assemblies 264 and/or 266 facilitate providing pressure on probe 100 to maintain surface contact during inspecting while still allowing movement of probe 100 relative to component 52. Accordingly, alignment assemblies 264 and/or 266 facilitate increasing the accuracy of the alignment process and the precision of the inspecting process. In the exemplary embodiment, alignment assemblies 264 and/or 266 are ball slides.

In operation, eddy current probe 100 is coupled to probe holder 240 as shown in FIG. 5. Specifically, probe tip portion 118 is inserted through bore 250 (FIG. 6) until probe base portion 120, particularly base portion first end 154, abuts probe holder upper surface 246. Moreover, when base portion 120 abuts probe holder 240, locating pin 162 is positioned adjacent shoulder 254, and as such is recessed below upper surface 246. In one embodiment, shoulder 254 includes a plurality of stops 268 that define a range of motion of locating pin 162. Specifically, eddy current probe 100 rotates around probe axis 260 until locating pin 162 contacts stop 268. In the exemplary embodiment, probe 100 has a circular path of travel and stops 268 are located approximately sixty degrees apart from one another. In another embodiment, stops 268 are located approximately one hundred and eighty degrees apart from one another. In yet another embodiment, probe assembly 60 does not include stops 268, and probe assembly 60 rotates three hundred and sixty degrees.

As shown in FIG. 6, extension arm upper surface 232 includes a plurality of scribe lines 270 to facilitate visually aligning eddy current probe 100 prior to scanning component 52. Specifically, base portion scribe line 164 is aligned with at least one of extension arm scribe lines 270 prior to scanning component 52. In one embodiment, prior to scanning, base portion scribe line 164 is right aligned such that scribe line 164 is substantially aligned with the right-most scribe line 270 of the extension arm 230. When inspecting component 52, probe 100 is rotated clockwise a predetermined amount, such as, but not limited to, sixty degrees until scribe line 164 is substantially aligned with the left-most scribe line 270 of extension arm 230. In another embodiment, scribe line 164 is center aligned prior to scanning component 52.

In use, probe assembly 60 is moveable between multiple inspecting portions of component 52. Specifically, once a portion of component 52 is scanned by eddy current probe 100, probe fixture 102 is removed from component 52 by adjusting adjustment mechanism 224 to move second leg 192 away from first leg 190 thereby releasing component 52. Probe fixture 102 is then repositioned on another portion of component 52, or another component to be inspected, and second leg 192 is readjusted by adjustment mechanism 224 until component 52 is pinched between first leg 190 and second leg 192. Once probe fixture 102 is secured, probe tip portion 118 is positioned adjacent component by actuating mechanism 242 such that the magnetic field generated by probe coil 140 is generated substantially perpendicular to a surface of component 52 being scanned. Specifically, in one embodiment, tip chamfer portion 130 extends parallel to and in contact with a portion of component 52 such as, but not limited to, the dovetail slot bottom chamfer region. Moreover, actuating mechanism 242 provides pressure on probe 100 to maintain contact between tip portion 118 and component 52 such that probe coil 140 is normal to the inspection surface. Once positioned, eddy current probe 100 is rotated such that probe coil 140 moves along component 52 for a predetermined distance. In one embodiment, probe coil 140 is moved in an arcuate path for a predetermined distance. Specifically, in another embodiment, probe 100 is positioned adjacent a break edge of a gas turbine engine disk. As such, tip chamfer portion 130 facilitates maintaining contact with the break edge and minimizing lift off as tip chamfer portion 130 has a substantially similar shape as the break edge. Accordingly, probe coil 140 maintains contact with component 52 throughout the scanning and/or inspecting of component 52. Once component 52 is scanned, the data accumulated is transferred to data acquisition/control system 62 (FIG. 2) via a connector 272 coupled to eddy current probe 100, and a cable 274 extending between connector 272 and data acquisition/control system 62. The data transmitted to data acquisition/control system 62 is then analyzed and recorded.

The above-described methods and apparatus provide a cost-effective and reliable means to facilitate reducing the amount time needed to perform an eddy current inspection on a component under test. Specifically, the method and apparatus described herein facilitates reducing an inspection time and improve an eddy current system performance by taking a continuous scan of a portion of the component from a fixed mount probe fixture. The probe assembly described herein includes an eddy current probe coupled to the probe fixture, and can therefore maintain consistent image quality, ensuring sensitivity.

Exemplary embodiments of digital eddy current proximity systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method for inspecting a gas turbine engine rotor disk, wherein the rotor disk includes a plurality of dovetail slots, said method comprising:
   providing a probe assembly including an eddy current probe and a probe fixture, wherein the eddy current probe includes a body portion and a tip portion including an eddy current probe coil, and wherein the probe fixture includes a platform, a first leg, and a second leg;
   inserting the eddy current probe into the probe fixture;
   coupling the probe fixture to the rotor disk such that at least a portion of the probe fixture is coupled to at least one of the dovetail slots and such that the eddy current probe is positioned adjacent the rotor disk, and such that at least one of the first leg and the second leg is slidably adjustable along the platform;
   generating an eddy current in the rotor disk using the eddy current probe coil; and
   inspecting the rotor disk using the probe assembly.

2. method in accordance with claim 1 wherein inspecting the rotor disk comprises rotating the eddy current probe within the probe fixture such that the tip portion is extended along the rotor disk for a predetermined distance.

3. A method in accordance with claim 1 wherein inspecting the rotor disk comprises rotating the eddy current probe within the probe fixture such that the tip portion travels in an arcuate path.

4. A method in accordance with claim 1 wherein at least one of the first leg and the second leg is moveable relative to the other leg, said coupling the probe fixture to the rotor disk comprises:
   positioning the probe assembly such that at least a portion of the rotor disk is between the first leg and the second leg; and
   repositioning one of the probe fixture legs closer to the other leg such that the portion of the rotor disk between the first leg and the second leg is securely coupled between the first and second legs.

5. A method in accordance with claim 1 wherein the probe fixture further includes an extension arm extending outwardly from the platform, and a probe holder coupled to the extension arm, said method further comprises coupling the eddy current probe to the probe holder.

6. A method in accordance with claim 5 wherein the probe holder includes a bore extending therethrough, said coupling the eddy current probe to the probe holder comprises positioning the eddy current probe within the bore such that the eddy current probe is rotatable within the bore.

7. A method in accordance with claim 5 wherein the probe holder includes an alignment assembly that facilitates aligning the probe holder relative to the rotor disk, said method further comprises coupling the alignment assembly between the extension arm and the probe holder such that the probe tip is positioned adjacent the rotor disk during scanning of the rotor disk by the eddy current probe.

8. A probe assembly for inspecting a gas turbine engine rotor disk, wherein the rotor disk includes a plurality of dovetail slots, said probe assembly comprises:
   an eddy current probe comprising a body portion, a tip portion extending from said body portion, an eddy current probe coil mounted within said tip portion, said tip portion is configured to be positioned adjacent the rotor disk such that said probe coil generates a magnetic field that is substantially perpendicular to a surface of the rotor disk being inspected; and
   a probe fixture configured to be coupled to at least one dovetail slot and to said eddy current probe such that said tip portion is positioned adjacent the rotor disk when said probe fixture is securely coupled to the at least one dovetail slot, said probe fixture comprises a platform, a first leg, and a second leg, at least one of said first leg and said second leg is slidably adjustable along said platform.

9. A probe assembly in accordance with claim 8 wherein the rotor disk includes a plurality of gear teeth extending outwardly from the rotor disk and defining the plurality of dovetail slots, said probe fixture is configured to couple to at least one of the plurality of gear teeth such that said tip portion is positioned within the dovetail slot.

10. A probe assembly in accordance with claim 8 wherein said probe fixture further comprises at least one leg extending outwardly from said platform, said at least one leg is configured to be inserted at least partially into the rotor disk for retaining said probe fixture in a fixed position relative to the rotor disk.

11. A probe assembly in accordance with claim 8 said first leg is fixed relative to said platform, said second leg is moveable relative to said platform, said first and second legs cooperate to securely couple a portion of the rotor disk therebetween.

12. A probe assembly in accordance with claim 11 wherein said probe fixture further comprises an adjustment mechanism coupled to at least one of said first leg and said second leg, said adjustment mechanism is configured to adjust a position of said second leg with respect to said first leg.

13. A probe assembly in accordance with claim 8 wherein said probe fixture further comprises an extension arm extending outwardly from said platform, said eddy current probe is coupled to said extension arm.

14. A probe assembly in accordance with claim 8 wherein said probe fixture further comprises an extension arm extending outwardly from said platform and a probe holder coupled to said extension arm, said eddy current probe is coupled to said probe holder.

15. A probe fixture for positioning an eddy current probe adjacent a rotor disk including a plurality of dovetail slots, wherein the eddy current probe includes an eddy current probe coil that is positionable adjacent the rotor disk for inspecting the rotor disk, said probe fixture comprises:
   a platform comprising a first surface and a second surface;
   an extension arm extending outward from said first surface, wherein the eddy current probe is coupled to said extension arm; and
   a first leg and a second leg each extending outwardly from said second surface such that at least one of said first and second legs is configured to be coupled to a portion of the rotor disk, at least one of said first leg and said second leg is slidably adjustable along said second surface.

16. A probe fixture in accordance with claim 15 wherein said first leg is fixed with respect to said platform, said second leg is moveable with respect to said platform, said first and second legs cooperate to securely couple a portion of the rotor disk therebetween.

17. A probe fixture in accordance with claim 15 further comprising an adjustment mechanism coupled to at least one of said first and second legs, said adjustment mechanism is configured to adjust a position of said second leg with respect to said first leg.

18. A probe fixture in accordance with claim 15 further comprising a probe holder and an alignment assembly coupled between said probe holder and said extension arm, wherein the eddy current probe is coupled to said probe holder, said alignment assembly facilitates retaining the eddy current probe in contact with the rotor disk while the probe inspects the rotor disk.

19. A probe fixture in accordance with claim 15 wherein the rotor disk includes a plurality of gear teeth extending outwardly from the disk to define the plurality of dovetail slots, said first leg inserted into a portion of a dovetail slot, said second leg configured to contact at least one gear tooth such that said probe fixture positions the tip portion of the eddy current probe against a bottom of the dovetail slot.

* * * * *

UNITED STATES PATENT AND TRADEMARK OFFICE
CERTIFICATE OF CORRECTION

| | | |
|---|---|---|
| PATENT NO. | : 7,190,162 B2 | Page 1 of 1 |
| APPLICATION NO. | : 10/898080 | |
| DATED | : March 13, 2007 | |
| INVENTOR(S) | : Tenley et al. | |

It is certified that error appears in the above-identified patent and that said Letters Patent is hereby corrected as shown below:

Column 8, line 50, delete "method in" and insert therefor -- A method in --.

Signed and Sealed this

Sixth Day of November, 2007

JON W. DUDAS
*Director of the United States Patent and Trademark Office*